(12) United States Patent
Russell et al.

(10) Patent No.: US 9,867,891 B2
(45) Date of Patent: Jan. 16, 2018

(54) DELIVERY DEVICE

(71) Applicant: SURFACESKINS LIMITED, Leeds, Yorkshire (GB)

(72) Inventors: Stephen John Russell, Oval Harrogate (GB); Simon Geoffrey John Scott Harden, Kenton Newcastle Upon Tyne (GB); Adam David Walker, Thorp Arch Wetherby (GB); Christopher Edward Fowler, York (GB)

(73) Assignee: SURFACESKINS LIMITED, Leeds Yorkshire (GB)

( * ) Notice: Subject to any disclaimer, the term of this patent is extended or adjusted under 35 U.S.C. 154(b) by 200 days.

(21) Appl. No.: 14/400,435

(22) PCT Filed: May 11, 2013

(86) PCT No.: PCT/EP2013/059755
§ 371 (c)(1),
(2) Date: Nov. 11, 2014

(87) PCT Pub. No.: WO2013/167746
PCT Pub. Date: Nov. 14, 2013

(65) Prior Publication Data
US 2015/0117932 A1    Apr. 30, 2015

(30) Foreign Application Priority Data
May 11, 2012  (GB) .................................. 1208282.2

(51) Int. Cl.
*A61L 2/18*    (2006.01)
*A61L 2/232*    (2006.01)
(Continued)

(52) U.S. Cl.
CPC .................. *A61L 2/18* (2013.01); *A61L 2/232* (2013.01); *B32B 5/022* (2013.01); *B32B 5/024* (2013.01);
(Continued)

(58) Field of Classification Search
CPC ...................................................... B32B 3/266
See application file for complete search history.

(56) References Cited

U.S. PATENT DOCUMENTS

| 4,832,942 | A | 5/1989 | Crace |
| 4,994,273 | A | 2/1991 | Zentner et al. |

(Continued)

FOREIGN PATENT DOCUMENTS

| DE | 3026258 | 1/1982 |
| DE | 10158286 | 11/2002 |

(Continued)

OTHER PUBLICATIONS

International Search Report for PCT/EP2013/059755, Completed by the European Patent Office on Aug. 27, 2013, 6 Pages.

*Primary Examiner* — Jennifer C Chiang
*Assistant Examiner* — Bradley Oliver
(74) *Attorney, Agent, or Firm* — Brooks Kushman P.C.

(57) ABSTRACT

A delivery device is described for intermittently delivering materials such as liquids or gels over a sustained period of time to a surface in a controlled way. The surface mountable delivery device is capable of delivering, for example, an antimicrobial agent to protect surfaces from microbial contamination and/or to disinfect surfaces, e.g. door handles, push plates, hand rails, etc. as an aid in preventing and/or hindering the spread of infectious agents. In one arrangement the device utilises a foam based reservoir in combination with a nonwoven fabric wicking layer and an elastomeric liquid delivery contact layer having valve like pore (Continued)

and/or slits; the combination provides for control of material delivery and longevity for the device in use.

39 Claims, 5 Drawing Sheets

(51) Int. Cl.
    *B32B 5/02*                       (2006.01)
    *B32B 5/24*                       (2006.01)
    *B32B 5/26*                       (2006.01)

(52) U.S. Cl.
    CPC ............... *B32B 5/245* (2013.01); *B32B 5/26* (2013.01); *B32B 2262/04* (2013.01); *B32B 2266/0278* (2013.01); *B32B 2266/06* (2013.01); *B32B 2307/728* (2013.01)

(56) References Cited

U.S. PATENT DOCUMENTS

| | | | |
|---|---|---|---|
| 5,407,685 A | 4/1995 | Malcheskly et al. | |
| 5,882,667 A | 3/1999 | Jones | |
| 6,262,331 B1 * | 7/2001 | Nakahata | A61F 13/49011 604/358 |
| 6,298,521 B1 | 10/2001 | Butterfield | |
| 6,319,510 B1 | 11/2001 | Yates | |
| 6,803,334 B2 | 10/2004 | Mizutani et al. | |
| 6,821,325 B1 | 11/2004 | Williams et al. | |
| 6,863,960 B2 | 3/2005 | Curro et al. | |
| 2002/0022427 A1 | 2/2002 | Curro et al. | |
| 2002/0041824 A1 | 4/2002 | Dawson et al. | |
| 2003/0203015 A1 | 10/2003 | Aledo et al. | |
| 2005/0034270 A1 | 2/2005 | Newman et al. | |
| 2007/0049894 A1 * | 3/2007 | Fitts, Jr. | B32B 3/266 604/385.22 |
| 2011/0111000 A1 | 5/2011 | Russell et al. | |

FOREIGN PATENT DOCUMENTS

| | | |
|---|---|---|
| DE | 20310052 | 10/2003 |
| EP | 2098664 | 9/2009 |
| FR | 2892025 | 4/2007 |
| GB | 2363075 | 12/2001 |
| GB | 2436284 | 9/2007 |
| GB | 2472188 | 2/2011 |
| WO | 2005061600 | 7/2005 |
| WO | 2007135424 | 11/2007 |

* cited by examiner

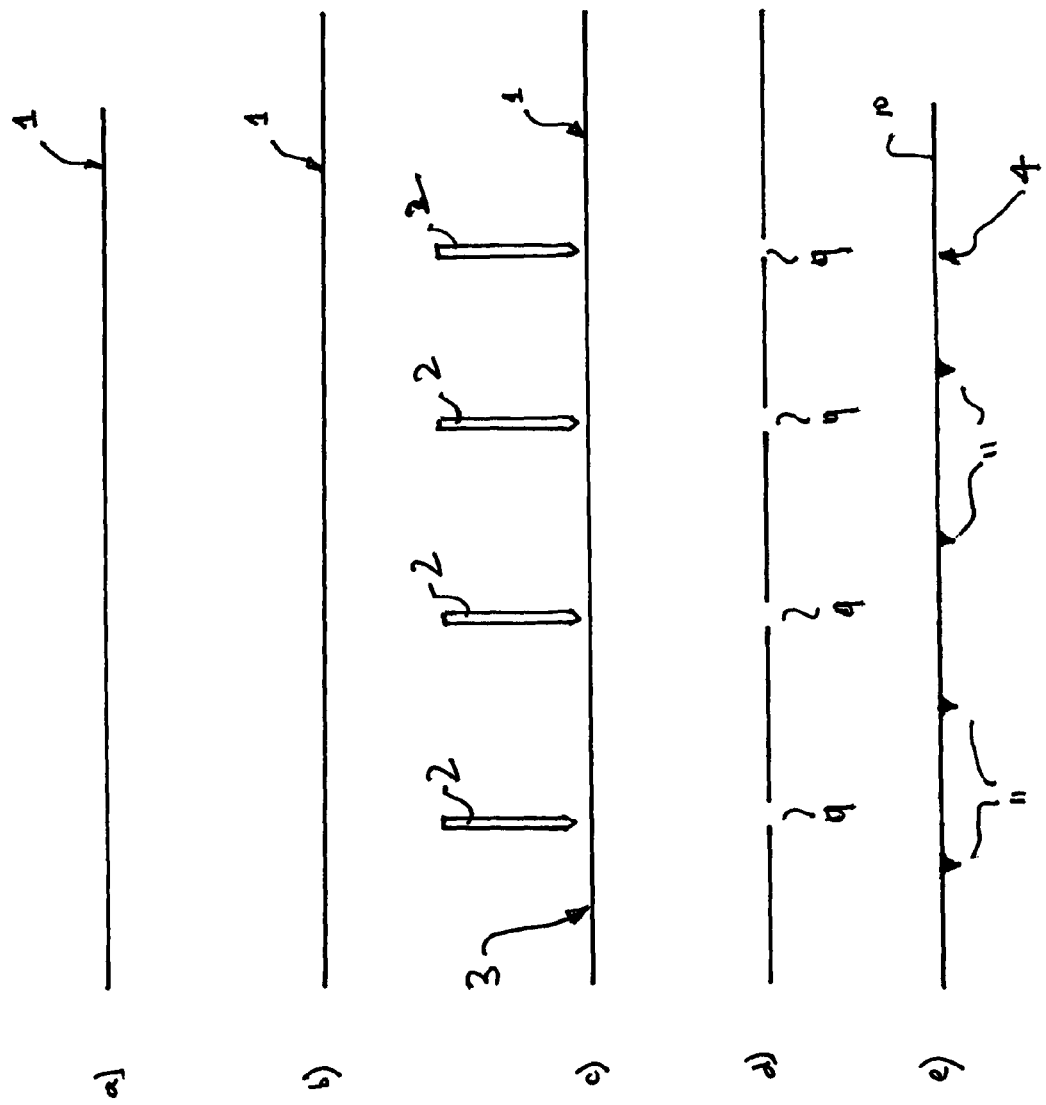

DELIVERY DEVICE

CROSS-REFERENCE TO RELATED APPLICATION

This application is the U.S. national phase of PCT Application No. PCT/EP2013/059755 filed on May 11, 2013, which claims priority to GB Patent Application No. 1208282.2 filed on May 11, 2012, the disclosures of which are incorporated in their entirety by reference herein.

FIELD OF INVENTION

The present invention relates to a means of delivering materials such as liquids or gels over a sustained period of time to a surface in a controlled way. In particular the invention provides a surface mountable delivery device capable of delivering, for example, an antimicrobial agent to protect surfaces from microbial contamination and/or to disinfect surfaces, e.g. door handles, push plates, hand rails, etc. as an aid in preventing and/or hindering the spread and transmission of infectious agents.

BACKGROUND ART

It is widely recognized that there is a major problem with the spread of infectious agents from one place to the next, as people/animals and organisms touch one surface and another. Infectious agents include microbes (microorganisms), e.g. bacteria, fungi (including spores), viruses or prions. Contact—hence the word "contagious disease" is the most common way that pathogens can spread from one individual to another. This transmission of microbes present on the hands/skin/body of people/organisms, are transferred onto the surfaces of items such as door handles/door knobs/door push plates/door rails/door leavers/counters/work surfaces/sinks/taps/car handles/towel/rails/bath rails/sink rails/stair lift rails/banisters, to name but a very small selection of surfaces that are frequently touched/contacted by a large number of individuals, in a short space of time. Such surfaces are then touched by the hands/skin/body of other person/organisms and these microbes may be picked up or transmitted by this new individual. If the microbe enters the human body via an open skin surface, such as a wound, e.g. a cut/abrasion, or by oral contact, there is potential for infection. Infections include those of the skin and other tissues, the bloodstream, the lungs and the urinary tract. Once in the body system, these pathogens can also lead to a cold, flu, mumps/measles, conjunctivitis, diarrhoea, bronchitis, dermatological disorders, vomiting or sickness, for example.

This is a particular problem in hospitals and medical centres, where the transmission of nosocomial infections or Healthcare Associated Infections (HCAIs), e.g. methicillin-resistant *Staphylococcus aureus* (MRSA), *clostridium difficile* (*C. diff*), norovirus by surface contact is a major cause of illness.

Infection control typically involves the prevention and control of healthcare-associated infections in primary and community care. Hospitals take steps to prevent the transmission of HCAIs to avoid infecting patients. Measures to prevent the spread of microorganisms from one person to another involve isolation or infection control. The type of infection control or isolation required for any patient depends, inter alia, on the microorganism, where the microorganisms are found on/in an individual and the patient. The most important type of isolation required for MRSA is what is called "contact isolation". This type of isolation requires everyone in contact with the patient to be very careful about hand washing after touching either the patient or anything in contact with the patient.

About 10% of infections in the UK's public hospitals have been estimated to be airborne. This means that approximately 90% of infections are therefore transmitted in other ways, such as through contact with surfaces and other individuals. A significant number of contact surfaces in hospitals and public buildings are vertical surfaces such as door touch plates.

Biosecurity is a term that covers the actions and measures needed to be taken to safeguard individuals from diseases caused by viral, bacterial and fungal infections. Biosecurity is essential against the fight of these contagious diseases. Thus, it is highly desirable to provide a means of reducing the spread of microorganisms, e.g. in, hospitals, (where surfaces are regularly touched by many people), doctors waiting rooms and doors, public houses including door handles and furniture, veterinary buildings and doors etc, as well as office equipment/computer keyboards/mice etc. A number of attempts have been made to address this issue as described for example in, U.S. Pat. No. 5,407,685, U.S. Pat. No. 5,882,667, U.S. Pat. No. 6,298,521, U.S. Pat. No. 6,863,960, EP2098664, FR2892025, GB2363075A, GB2436284A, GB2472188A, U.S. Pat. No. 4,832,942, US published application US2002041824A1, and US published application US2005034270A1.

U.S. Pat. No. 6,821,325 describes a multi-surface antibacterial protective device comprising, an under layer of material and an over a layer of a permeable material and a cavity disposed between the two. The cavity houses an antibacterial solution. There is little or no control over the seepage of the antibacterial agent from the cavity and when a liquid is used in the cavity, settlement of the liquid to the bottom of the system occurs, particularly when it is oriented vertically in use. Failure to address settlement causes a variation in the amount of liquid delivered from top to bottom, which becomes more pronounced as the system is progressively emptied of solution. Clearly, such a variation in the delivery rate across the system is a major concern where the system is applied to walls and door plates.

Published International application WO2007135424A1 describes a surface mountable delivery device, which has a multi layer construction comprising a liquid permeable support layer adjacent to a porous reservoir layer, the porous reservoir layer being provided with a backing layer. The surface mountable delivery device may comprise of stickers, tapes, pads, tubes, socks, etc. The present invention seeks to address in part the shortcomings with the device of U.S. Pat. No. 6,821,325, whilst improvement has been achieved by the device disclosed in WO2007135424A1 there remains a need for further or alternative devices.

A number of prior art devices that have a discrete porous contact surface through which material may be discharged are problematic during use. When their contact surfaces are contacted or compressed by for example a human hand liquid or gel may be discharged through the majority of the contact surface, even where no actual contact has occurred. There is little control or localisation of material discharge. This results in discharge of material beyond that required to be discharged at the point of contact, where disinfectant is required. This can often result in liquid run-off or dripping from the surface of the device. This is wasteful of disinfectant and results in a need to replace the device more frequently than is desirable.

In addition a further problem with prior art devices is that significant liquid evaporation occurs during use as there is difficulty in controlling or preventing evaporation from porous contact surfaces. This is particularly problematic when the liquid or gel consists of a volatile material such as an alcohol, e.g. ethanol.

DISCLOSURE OF THE INVENTION

According to a first aspect of the invention there is provided a delivery device, comprising a reservoir of porous material in communication with a liquid delivery contact layer, wherein the reservoir material has a compression modulus within the range of 150 to 650 $N \cdot m^{-2} \cdot \Delta mm^{-1}$ and most preferably from 250-350 $N \cdot m^{-2} \cdot \Delta mm^{-1}$. Compression modulus in the context of this aspect of the present invention relates to the resistance to permanent or semi-permanent reduction in material thickness with applied pressure.

Compression modulus is determined by taking a sample of the material of known thickness (typically within the range of 5 to 10 mm) and applying known weights (typically between 20 to 200 g) to the surface of the porous material e.g. foam, which is compressed when the weight is deposited on the material surface. The weight is applied over an area of $5.03 \times 10^{-3}$ $m^2$ for a period of 10 seconds after which the weight is removed and the material thickness is determined using a Shirley thickness gauge and compared to the thickness of the material prior to application of the weight.

The porous reservoir material should have a compression modulus that is not so high as to effectively prevent compression of the porous reservoir material during use in a delivery device with the resultant controlled displacement of compositions, such as cleaning fluids or gels, from the porous reservoir material e.g. foam. In addition the porous reservoir material should not have a compression modulus that is too low. A low compression modulus would result in excessive displacement of compositions from the porous reservoir material as it would be susceptible to a large decrease in material thickness under relatively low forces and especially under the typical forces observed during use.

The porous reservoir material may be any porous material with the requisite properties and should have an interconnected pore network wherein individual pores are connected to others such that liquids can easily flow through the entire structure, displacing air that may be present. It may be a woven or nonwoven porous material or a foam or any combination of two or more of these materials. The porous reservoir may comprise a composite material and/or may comprise a multilayer material. Preferably the porous reservoir material comprises one or more layers of porous material and preferably comprises one or more layers of foam material, preferably an open cell foam, e.g. reticulated foam. Preferably the porous reservoir material comprises a hydrophilic polyurethane open cell foam. Preferably the porous reservoir material comprises two or more layers of porous material and preferably comprises two or more layers of a hydrophilic polyurethane thermoset foam. Preferably the two or more layers of porous material are of the same thickness. One example of a suitable foam is Type 562-B as manufactured and supplied by Rynel Ltd. Co., Boothbay, U.S.A. Other suitable and preferred foams are those as described and prepared in WO 2005061600, the complete disclosure of which is hereby incorporated by reference. Thus the foam may be a low-density, open-cell, thermoplastic, absorbent foam, comprising at least two of the groups consisting of: a base resin, a surfactant, a thermoplastic elastomer, and a plasticizing agent and may be made by a method comprising the steps of: providing a foam polymer formula including the base resin, the plasticizing agent, and the surfactant; heating the foam polymer formula to create a polymer melt utilizing a blowing agent; foaming the polymer melt to a density of about 0.1 g $cm^{-3}$ or less; and extruding the polymer melt to form an open-cell, soft, flexible, thermoplastic, absorbent foam.

Preferably, the porous reservoir material has a void fraction of greater than 80%, preferably greater than 85% and most preferably greater than 90% as determined by gas pycnometry. Preferably the porous reservoir material has a density of 0.2 g $cm^{-3}$ or less, more preferably 0.15 g $cm^{-3}$ or less and most preferably 0.10 g $cm^{-3}$ or less as determined by ASTM D1622-98. The thickness of the porous material comprising the porous reservoir may be greater than 10 mm. Preferably the total thickness of the porous material comprising the porous reservoir is less than 12 mm, preferably less than 11 mm and most preferably less than 10.5 mm. Most preferably it is within the range of 7 to 10 mm with a Coefficient of Variation of less than 5%. Typically and preferably the reservoir material will have pores that are equally aligned in all planes x, y and z.

Preferably the porous reservoir material has a relatively high resiliency in combination with a compression modulus within the range of 150 to 650 $N \cdot m^{-2} \cdot \Delta mm^{-1}$ and most preferably from 250-350 $N \cdot m^{-2} \cdot \Delta mm^{-1}$.

Preferably the resiliency as determined by ASTM D3575 is greater than 85%, more preferably greater than 90%, more preferably greater than 95% and most preferably within the range of 99-100%.

Preferably the porous reservoir material exhibits a percentage strain as measured at 6.8 KPa by the method described in ASTM D3575 of 30% or less preferably 28% or less and most preferably 27%.

Preferably the porous reservoir material has a mean flow pore diameter within the range of 80 to 400 microns.

In a preferred embodiment of this aspect of the present invention the delivery device may further comprise a wicking layer as hereinafter described in the second aspect of the present invention and/or may comprise an elastic liquid delivery contact layer as hereinafter described in the third aspect of the present invention. The porous reservoir preferentially has a high capillarity as this is especially advantageous when the device is in use in a vertical position.

It is preferred that the capillarity of the wicking layer is greater than that of the porous reservoir. In a further alternative the porous layer may comprise a plurality of chambers each containing a porous material as hereinbefore described. The porous reservoir layer may preferably be contiguous with the wicking layer, which preferably is adjacent to and may be contiguous with the liquid delivery contact layer.

The liquid delivery contact layer may be a liquid permeable or impermeable film or membrane. Preferably the contact layer is made of liquid impermeable material. The film may be a porous film or a perforated film, e.g. a micro perforated film. The liquid delivery contact layer is preferentially, a microperforated film. A variety of films may be used, thus, the film may be selected from any conventionally known film-forming polymers or blends thereof. Preferably, the film will be elastomeric and therefore have elastic properties, i.e. preferably a high elastic recovery (>75% at 1% extension). Preferably the film will be compatible with well known printing techniques. Also, the film will be non-degradable and/or soluble in water or when in contact with an alcohol or an oil-water emulsion. It is especially importantly that the printed surface should be insensitive to alcohol, e.g. ethanol, which forms the basis of many commercially available antibacterial formulations.

Thus, the liquid delivery contact layer may be hydrophobic polymer, such as polyurethane (PU), polyethylene (PE), polypropylene (PP), polyamide (PA), polyethylene terephthalate (PET), polysiloxane, vinyl methyl silicone, chlorosulphonated polyethylene, ethylene propylene diene monomer (EPDM), ethylene propylene and copolymers thereof. The liquid delivery contact layer may comprise of a bi-layer in which the upper and lower layers are formed from different polymers. One preferred material for the liquid delivery contact layer is a polyurethane and preferably an elastomeric polyurethane film.

The perforations in the liquid contact layer as slits and/or pore openings may vary depending, inter alia, upon the nature and composition of the antibacterial formulation present in the porous reservoir layer. Thus the slits and/or pores of the microperforated film may consist of sub-micron dimensions, however, preferentially, a microperforated film with openings of from 20-500 μm diameter (as measured across their minor axis) may be used, that is for example more than 50% of the pores have a diameter in the range of from 20-500 μm, preferably more than 70%, more preferably more than 90%. It is particularly advantageous if the liquid delivery contact layer, e.g. the perforated film is elastic so that the slit and/or pore openings may further open to their maximum extent due to the forces introduced by the user on this surface during use and the displacement of the liquid/gel from the porous reservoir layer and then self-close by elastic recovery of the film when the forces are removed from the system and the liquid flow ceases. Nevertheless, it should be understood that perforated high modulus films may also be suitable. Furthermore, it may be advantageous for each of the layers in the multi layer device to possess elastic properties.

In a preferred embodiment of this first aspect of the present invention the liquid delivery contact layer is in accordance with the third aspect of the present invention and comprises closed slits and/or pores.

According to a second aspect of the present invention there is provided a delivery device, comprising a reservoir in communication with a wicking layer separating the reservoir from a liquid delivery contact layer in communication with the wicking layer.

The use of the wicking layer in this device has two important functions. The first is to moderate or reduce the forced flow rate of liquid/gel from the reservoir to the liquid delivery contact layer and thereby control the volume of liquid delivered to that layer. The second is to act as a liquid distribution and wicking layer, which equalises the concentration of liquid across the working area of the device such that liquid is uniformly distributed immediately adjacent the liquid delivery contact layer even when acted upon by gravity. The reservoir layer is compressible and may see as much as a 50% reduction in volume when compressed, (i.e. 10 mm+can be reduced to <5 mm when compressed). Some of the liquid is forced out of the reservoir in to the wicking layer when the device is compressed. This is possible because the reservoir consists of interconnecting pores that communicate with the surface of the material of the reservoir layer. Some of the liquid expelled from the reservoir will be forced in to the wicking layer. However, because the wicking layer is thin compared to the reservoir and the rate of forced flow in to the wicking layer is high, the wicking layer reaches absorbent capacity quickly and any excess liquid will then pool in the bottom of the device. As the user removes the pressure from the device, this excess liquid is then reabsorbed back in to the reservoir and the wicking layer. Thus this function is to moderate the total volume of liquid that is transported to the contact layer when the delivery system is activated by the user. The wicking layer acts a flow resistor when forced flow of liquid is induced. When the delivery system is compressed by the user, liquid can be expelled from the reservoir and transported through the thickness of the wicking layer toward the contact layer. Drag forces created as the liquid passes around the multiple fibre surfaces in the wicking layer generate drag forces that resist the flow in this direction. The flow resistance induced by the wicking layer (through-thickness) ensures that excess fluid is not transported out of the delivery system on each activation. This ensures a more effective and efficient use of the liquid agents used with the device.

Preferably the wicking layer comprises porous material. Preferably the wicking layer comprises a woven or nonwoven fabric, most preferably a nonwoven fabric. The porous material of the wicking layer is preferably comprised of a pore structure that is capable of retaining and distributing in-plane (i.e. in the x and y planes), the cleaning fluid/gel by means of capillary forces. The predominant direction of fibre orientation in the porous wicking material is preferably aligned with the longitudinal axis of the delivery device, with preferably greater than 80%, more preferably greater than 90% of the pores aligned in the x-y plane. When the device is compressed, the porous material of the wicking layer is such that it restricts or moderates the total volume of cleaning fluid/gel that may be evacuated from the reservoir and passed transversely through the wicking layer and to the exterior of the device via the liquid delivery contact layer. In this way, over-delivery of cleaning fluid/gel to the exterior surface of the liquid delivery contact layer is reduced or prevented.

When the wicking layer comprises a woven or nonwoven fabric the transverse flow resistance of the wicking layer is partly influenced by the total surface area of the constituent fibres, which may be adjusted by selecting fibres having different diameters and/or cross-sectional shapes.

It is preferred that the wicking layer comprises fibre surfaces that are wettable, by the composition to be dispensed by the device e.g. cleaning fluids or gels and the like. In a preferred embodiment when the composition is aqueous the fibre surfaces are hydrophilic. Preferably the wicking layer has a sessile drop angle of less than 90° and more preferably less than 30°.

Suitable wicking materials include those composed of regenerated cellulose (specifically viscose, wood pulp, lyocell or Tencel®) which may be blended with synthetic materials (specifically PET, PA, PLA, PP or PE), wherein the synthetic component represents less than 40% by weight of the entire wicking material; plasma-treated aromatic and aliphatic polyesters and polyolefins; and blends thereof.

It is preferred that the wicking layer is a nonwoven fabric comprising a proportion of hydrophilic fibres or hydrophobic fibres that are surface modified using any method known in the art (e.g. plasma treatment, fibre finish, masterbatch additives) to enable them to be wetted by water and alcohol formulations (the latter including ethyl alcohol, i.e. ethanol). Inherently hydrophilic fibres in the art are composed of natural materials such as cellulose in native fibre form, e.g. cotton, flax, hemp, ramie, etc. or cellulose in regenerated form, e.g. lyocell (Tencel), viscose rayon, etc.

Preferably the wicking layer is a nonwoven fabric formed using a drylaid web formation method, such as carding wherein the fibre orientation can be controlled during production to enable the directional permeability and capillarity of the structure to be adjusted if required. In a particularly preferred embodiment, the fabric is produced from parallel-laid carded webs or cross-lapped carded webs wherein there is preferential fibre orientation in the machine direction (parallel-laid carded webs) or the cross-direction (cross-lapped webs) after bonding.

Bonding is accomplished by a mechanical bonding technique. Suitable mechanical bonding techniques include hydroentangling (spunlace) and needlepunching or combinations thereof. Furthermore, the resulting fabrics preferably exhibit anisotropy in both permeability and capillarity as a result of preferential fibre orientation in one or more directions. Most preferably this is in the x-y plane of the wicking layer. When assembled in to the delivery device, the direction of predominant fibre orientation in the fabric is aligned with the long axis of the device, or depending on orientation of the device in a suitable direction to oppose gravity.

An embossed pattern may be applied to the fabric as part of the hydroentangling process producing areas of variable density. This is achieved by means known in the art using structuring support surfaces in the machine. A honeycomb pattern is particularly preferable in assisting with liquid distribution, since the differences in density also result in different permeabilities and capillary pressure.

A particularly suitable and preferred material is a nonwoven fabric comprised of 100% Tencel® fibre prepared by carding, cross-lapping followed by needle punching. Preferably, this fabric has a mean thickness of between 0.5 and 2.0 mm, more preferably 1.0 to 2.0 mm. Preferably, 100% Tencel 1.7 dtex (linear density), 38 mm (mean fibre length), basis weight of the fabric: 80-100 g/m$^2$.

Another preferred material is a 65% Viscose rayon/35% Polyester, 100 g/m$^2$, having thickness range: 1-2 mm. The fabric is produced by carding wherein the webs from two or more carding machines are deposited one on top of the other (without cross-lapping) and then mechanically bonded by hydroentangling.

Preferably the nonwoven fabric has a bubble point pore diameter of between 50 to 100 μm, more preferably 60 to 90 μm, more preferably 70 to 80 μm and most preferably about 75 μm.

A Preferably the nonwoven fabric has a mean flow pore diameter of between 15 and 30 μm, more preferably 20 to 25 μm and most preferably about 23 μm.

It is preferred that the wicking layer is from 0.5 to 3.0 mm in thickness, more preferably 0.5 to 2.5 mm in thickness and most preferably 1 to 2.0 mm in thickness.

Preferably the wicking layer material has a mean flow pore diameter of between 10 to 100 microns.

The liquid delivery contact layer used in the second aspect of the present invention may be as described in relation to the first aspect of the present invention and preferably is in accordance with the liquid delivery contact layer of the third aspect of the present invention and comprises closed slits and/or pores.

In this second aspect the reservoir layer may preferably comprise a variety of porous materials, such as one or more of a foam, a woven material or nonwoven material; although a foam material is preferred. The porous reservoir may comprise a composite material and/or may comprise a multilayer material. A nonwoven material may be composed of a variety of materials, such as, cellulose pulp or other absorbent fibrous material, capable of holding liquid within and between the pores of adjacent fibres. The porous reservoir preferentially has high capillarity, as characterized by a wicking height of over 10 mm, most preferably over 50 mm (test medium: water) when the material has its largest dimension in the vertical orientation, as this is especially advantageous when the device is in use in a vertical position. In a further alterative the porous layer may comprise a plurality of chambers each containing a porous material as hereinbefore described. The porous reservoir layer may preferably be contiguous with the wicking layer, which preferably is adjacent to and may be contiguous with the liquid delivery contact layer.

In a preferred embodiment of this second aspect of the present invention the reservoir material is as used in accordance with the first aspect of the present invention and is preferably a foam material.

According to a third aspect of the present invention there is provided a delivery device, comprising a reservoir in communication with a wicking layer, separating the reservoir from an elastic liquid delivery contact layer in communication with the wicking layer, the elastic liquid delivery contact layer having a plurality of closed slits and/or pores.

The elastomeric nature of this layer in combination with the use of closed slits and/or pores and material selection for the layer has distinct benefits for the devices of the present invention. The elastic liquid delivery contact layer of the present invention has two important functions.

Firstly, the elastic liquid delivery contact layer is generally a dry-state, non-porous and non-permeable elastomeric film material. In place of the pores of the prior art, which are open structures the film of the present invention preferably comprises closed slits and/or pores. The elastic liquid delivery contact layer with these properties acts as the final barrier between the reservoir in the interior of the device, which contains cleaning fluids or gels that incorporate volatile fluids (e.g. alcohol) and the exterior of the device. The contact layer controls the evaporation of cleaning fluids or gels that incorporate volatile fluids. Typical prior art devices with open porous layers lose significant quantities of volatile fluids from their reservoirs via evaporation and have seeping or wet-state contact layers, which are not desirable. The elastic liquid delivery contact layer of the present invention prevents this evaporation and fluid loss through use of a non-porous non-permeable film with closed slits and/or pores and thus ensures that there is no significant seeping from the device and the contact surface remains dry.

Secondly, the elastic liquid delivery contact layer, as the final barrier between the reservoir and the exterior of the device, must also be able to allow the cleaning fluids or gels that incorporate volatile fluids to pass through it and to the exterior surface of the layer. This is typically achieved in the prior art by the introduction of open pores or relatively open pores that enable quantities of cleaning fluids or gels that incorporate volatile fluids to pass through the layer but have the disadvantage of providing an evaporation pathway through the layer. The elastic liquid delivery contact layer of the present invention having a plurality of closed slits and/or pores overcomes this problem. A slit in this context is defined as a rectangular rather than substantially cylindrical opening such that the edges are capable of communicating when the material is in an unstrained state. When in position for use but without any applied pressure to the surface of the device the slits and/or pores of the contact layer are closed. In the closed non-impact state, and due to their method of manufacture, the layer material at the slit site is distorted effectively forming an overlapping and puckered arrangement closing the slit. In this position evaporation through the layer is significantly reduced compared to that observed with conventional porous layers because the two edges of the slit remain in communication closing the slit. With slits the separation of the adjacent parallel edges of these slits to open the closed slit is induced by mechanical force or shear induced in the elastic liquid delivery contact layer during use when the layer is contacted or impacted by a human hand. Thus at the point of need and only at that point the slits are open and allow the passage of cleaning fluids or gels from the reservoir to through the layer and to the contacted surface of the layer. This slit opening mechanism is a localized mechanism, meaning that areas in the contact layer that are remote from the point of contact are relatively unaffected when other slits are being opened during use. This means that slits remote from the impact site on the layer remain closed or relatively closed compared to those at the site of impact. This mechanism ensures that the maximum flux of cleaning fluids or gel through the layer is at the point of contact. When the applied force of contact or impact is removed from the liquid delivery contact layer the opened slits return to their original closed position and function; the elastic recovery of the layer re-introduces the material distortion and puckering at the slit site closing the slit. With closed pores a similar mechanism occurs. In the closed non-impact state, and due to its method of manufacture, the layer material at the pore site is distorted effectively forming an overlapping and puckered arrangement closing the pore. On impact in use this region of the layer is elastically deformed and the distortion and puckering is temporarily removed to open the pore. When the contact pressure is removed the elastic recovery of the layer re-introduces the material distortion and puckering at the pore site closing the pore.

The elastic liquid delivery contact layer is fixed at its outer extremities to a rigid member so that when force is applied substantially perpendicular to the surface of the unfixed areas, the layer is partially elongated to accommodate the perpendicular displacement. This elongation of the film causes a temporary separation of the adjacent parallel edges of any slits and/or pores that are in the vicinity of the applied force. The adjacent edges return to their original position after the force is removed in order that the film remains substantially impermeable to liquid or gas in ambient conditions.

The slits and/or pores may be arranged in any fashion within the liquid delivery contact layer. They may be arranged in a parallel fashion either from top to bottom of the device or from side to side of the device within the liquid delivery contact layer. The slits may be arranged in a twill pattern.

Preferably to ensure that the parallel edges of the slits remain in the closest proximity, no stored strain is present in any direction within the layer after its integration into the device; this is especially beneficial when the slits are arranged in a twill fashion Preferably, there is no pre-strain transverse to the slot length after its integration into the device. In some embodiments an amount of pre-strain of preferably 0.2%-5% of the relevant dimension in the layer in a direction parallel to the slot length may be advantageous in ensuring tight closure of the slots through additional contact pressure induced at the parallel slot edges.

Any non-permeable non-porous elastic material may be used as the elastic liquid delivery contact layer material. Preferably the layer is manufactured from an elastomeric polymeric material. By non-permeable is meant non-permeable to the typical components of the compositions located within the reservoir and used in the manufacture of cleaning fluids or gels that incorporate volatile fluids. The material may be a hydrophobic polymer, such as polyurethane (PU), polyethylene (PE), polypropylene (PP) or polyethylene terephthalate (PET) and copolymers thereof. The liquid delivery contact layer may comprise of a bi-layer in which the upper and lower layers are formed from different polymers. The preferred material for the liquid delivery contact layer is an elastomeric polyurethane material.

Preferably, the elastomeric film material has a maximum extension that is below the elastic limit of the layer material in order that on release of the impact force, up to 100% elastic recovery takes place so that the original positions of the slit edges and form of the slit are regained. This facilitates repeated, cyclic separation and recovery of the original slit edge positions and form. Closed pores are also able to return to their original pre-impact state.

The elastomeric film preferably exhibits a maximum extension of 500%-850% and a peak load at 20% extension of between 5 to 15 N/25 mm and more preferably 7.5 to 12.5 N/25 mm and most preferably about 10 N/25 mm.

The breaking load of the film is preferably not less than 20 N/25 mm, more preferably not less than 30 N/25 mm and most preferably not less than 40 N/25 mm (8 MPa).

The elastomeric film is preferably less than 1000 microns in thickness, more preferably less than 800 microns in thickness, more preferably 50 to 1000 micron in thickness, more preferably 50 to 800 microns in thickness, more preferably 50 to 500 microns and most preferably 50 to 300 microns.

One preferred class of elastomeric materials for use as the elastic liquid delivery contact layer include those consisting of polyurethane (PU). A preferred example being a white elastic film K 6104.040 (Nordenia, Germany), which has a thickness of 200 microns (DIN 53 370). A further preferred class of materials includes thermoplastic polyester elastomeric films that have a Shore D hardness of >60. These have been found to be particularly suitable for sublimation printing. A preferred example of thermoplastic polyester elastomeric materials include Hytrel® 6356 (DuPont).

The number of slits per square area in the elastic layer is preferably between 40 to 150 slits/in$^2$ (6.2 to 23.3 slits/cm$^2$), more preferably 50 to 140 slits/in$^2$ (7.8 to 21.8 slits/cm$^2$), more preferably 60 to 130 slits/in$^2$ (9.3 to 20.2 slits/cm$^2$), and most preferably 63 slits/in$^2$ (9.8 slits/cm$^2$)–126 slits/in$^2$ (19.5/cm$^2$). It is preferred that the slit length is 5 mm or less, more preferably 4 mm or less, more preferably 3 mm or less and most preferably 1.5 mm or less. Preferably the slits are within the range of 0.1 mm to 1 mm in length. The width of the slits is ideally as small as possible so that opposing sides of the slits are in contact when the elastic layer is not under any applied stress during use. There may be a small amount of separation and this may result in a slit width, which is preferably within the range of 5 to 200 μm, preferably 5 to 150 μm, more preferably 10 to 150 μm, more preferably 15 to 150 μm, more preferably 20 to 150 μm and more preferably less than 100 μm, more preferably less than 50 μm and most preferably less than 20 μm. Closed slits are preferred to closed pores but the elastic liquid delivery contact layer of the present invention may comprise slits and/or pores. When closed pores are present they may be present in the same pore density as described for slits.

The slits may be imparted to an elastomeric film through use of a cutting tool that that has a plurality of blades that may be impressed into and cut through the elastomeric film, such as a stamp press. This may be undertaken in a continuous fashion by feeding a web or elastomeric film into an engraved or toothed slitting roller. Pores when introduced may be introduced by a suitable pin arrangement on for example a stamp press that punctures the film. The elastomeric film is designed to limit the evaporation of a 62% ethanol in water composition to a maximum of 5% after five days exposure in an environment of 21° C. and 65% RH.

In this third aspect the reservoir layer may preferably comprise a variety of porous materials, such as one or more of a foam, a woven material or nonwoven material; although a nonwoven material may be preferred. The porous reservoir may comprise a composite material and/or may comprise a multilayer material. Such a nonwoven material may be composed of a variety of materials, such as, cellulose pulp or other absorbent fibrous material, capable of holding liquid within and between the pores of adjacent fibres. The porous reservoir preferentially has a high capillary action as this is especially advantageous when the device is in use in a vertical position. In a further alterative the porous layer may comprise a plurality of chambers each containing a porous material as hereinbefore described. The porous reservoir layer may preferably be contiguous with the permeable support layer.

In a preferred embodiment of this third aspect of the present invention the porous reservoir material is in accordance with the first aspect of the present invention and is preferably a foam material.

In a preferred embodiment of this third aspect of the present invention the wicking layer is in accordance with the second aspect of the present invention.

In a preferred embodiment of this third aspect of the present invention the elastic liquid delivery contact layer is in accordance with the fifth aspect of the present invention.

In respect of all aspects of the present invention the elastic liquid delivery contact layer is preferably printed or otherwise coloured. It is preferable that such printed or colouring of the surface is fast (resistant) to the cleaning fluid/gel components contained within the assembly, including alcohols. Emblems, motifs, brands, health messages and advertising information can be applied to the surface of the elastic liquid delivery contact layer by printing.

It has been found that printing of the polyurethane elastomeric material is particularly challenging. In a further aspect of the present invention to facilitate printing the polyurethane film can be subjected to pre-heating prior to the printing stage to drive out moisture. Preferably the pre-heating is at a temperature within the range of 150 to 180° C., more preferably 160 to 180 ° C. and most preferably at up to 170 ° C.±5° C. It is preferred that the pre-heating is for between 2 to 40 seconds, more preferably, 5 to 30 seconds, more preferably 10 to 25 seconds and most preferably at about 20 seconds 170 ° C.±5° C. The pre-heated film is cooled prior to printing. The pre-heating may be omitted if there is no moisture present that could inhibit the printing process. In a preferred process the elastomeric film layer is printed prior to slitting and/or perforating.

To ensure long-term stability and high clarity images, printing is most preferably achieved by ultraviolet (UV) printing, which relies upon the application of UV-curable inks to the surface of the polyurethane film.

According to a fourth aspect of the invention there is provided a delivery device, comprising a porous reservoir, having liquid retained therein, in communication with a liquid delivery contact layer, wherein the liquid content of the porous reservoir is less than 80% by volume of the total capacity of the porous materials selected for the reservoir. Preferably the liquid content of the reservoir is 60% or less by volume.

In a preferred embodiment of this fourth aspect the porous reservoir material is in accordance with the first aspect of the present invention, the device comprises a wicking layer in accordance with the second aspect of the present invention and the liquid delivery contact layer is in accordance with the third aspect of the present invention.

In a fifth aspect of the present invention there is provided an elastomeric film having valve like pores and/or slits and a method for manufacturing such a film. Thus the present invention provides a method for the manufacture of an elastomeric film with valve like pores and/or slits, which method comprises applying a strain to an elastomeric material, while the elastomeric material is under strain inducing a plurality of pores and/or slits through the elastomeric material, and removing the applied strain to enable the elastomeric material to elastically recover closing the pores and/or slits. In a preferred embodiment the applied strain is below 20% strain, preferably below 15% strain, more preferably below 10% strain and most preferably between 1 and 10% strain. The present invention further provides an elastomeric film having valve like pores and/or slits obtained or obtainable by this process. The process in using elastomeric material under strain ensures that the pores and/or slits have a certain dimension; when the strain is removed the elastomeric film with pores and/or slits relaxes under elastic recovery and the pores and/or slits and the material around them contract with this recovery to a smaller dimension and to a closed state with localized distortion of layer material around the pores and/or slits. In this closed state these pores and/or slits may act as valves; closed when the film is relaxed and opened when the film is under strain. Such films may be used with one or more of the various aspects of the present invention disclosed herein or may find use in other applications. The elastomeric film used in this aspect may be as described in other aspects of the present invention. The valve like pores and/or slits may have a specific form due to the method of manufacture and not seen with conventional slitting and/or puncturing. This takes the form of excess material around the slit or pore site that protrudes from the surface of the film in the relaxed state. The film essentially has two major surfaces. When the film is slit or punctured under extension the slitting or puncturing device contacts one of these major surfaces, pushes through the film material and on puncturing the film material is exposed at the other film surface. When the slitting or puncturing tool is removed and the film is relaxed excess film material associated with the slit and/or pore protrudes from the surface of the film that is remote from that contacted by the slitting and/or puncturing tool. It is this protruding excess material in combination with the films elastic properties that provides the valve like function to the slits and/or pores. The protruding excess slit and pore material may be located on the contact surface of the elastic contact layer or may be located on the surface that faces inwards into the device and towards the reservoir or wicking layer when present. It is preferred that the protruding excess slit and pore material is on the inwards facing surface so as not to interfere with the printing of the contact surface. In a preferred embodiment the layer comprises slits and not pores.

The prior art devices that include a porous reservoir material require that this material be saturated with the cleaning fluids or gels. However, these devices suffer to varying degrees with pooling of cleaning fluids or gels towards the bottom of the reservoir chamber when these devices are attached to a vertical surface. Counter intuitively it has been found that if the porous reservoir is under-filled with cleaning fluids or gels below its total absorption capacity then not only is pooling avoided but the device is able to deliver more cleaning fluids or gels at effective locations during use of the device.

In all aspects of the present invention a backing layer or container may be provided to the device that prevents penetration of active liquid there through and which prevents evaporation. This container or backing layer is preferably a non-porous and non-permeable film composed of a hydrophobic polymer. Exemplary hydrophobic polymers include polyethylene (PE), polypropylene (PP) or polyethylene terephthalate (PET) and copolymers thereof. This container may be molded, formed, cut, injection molded, vacuum formed, thermoformed, die-cut or formed through other methods. The material used has good vapour barrier properties; suitable materials include PET, APET, RPET, PP, PE, HDPE, ABS and similar materials.

The device of the invention may include means for attaching the device to a surface. This may comprise an attaching means arrangement or may comprise one or more adhesive surfaces. The delivery device may by design be arranged to attach to a surface or to attach to itself, by wrapping around a surface. In a preferred embodiment the attaching means comprises an adhesive, for example, the backing layer is coated or substantially coated with an adhesive layer, e.g. a pressure-sensitive adhesive, to enable fixation of the surface mountable delivery device to various surfaces. Such an adhesive layer may be applied to the backing layer or alternatively the backing layer may itself comprise an adhesive provided that such an adhesive is contiguous over the surface of the porous layer and prevents penetration of active liquid through and which prevents evaporation. The adhesive is preferably a pressure sensitive adhesive which may optionally be alcohol soluble, thus enabling it to be removed from surfaces when the delivery device of the invention is removed. The pressure sensitive adhesive may be an acrylic adhesive such as an acrylate ester copolymer adhesive formed by the copolymerization of 2-ethyl-hexyl acrylate, butyl acrylate and acrylic acid. Alternatively, the adhesive layer may be an adhesive such as polyvinyl alkyl ether adhesive.

In all aspects of the present invention it is preferred that the liquid permeable first layer and the container or backing layer may be capable of thermoplastic bonding, e.g. ultrasonic, radio frequency joining and heat welding.

In use, the devices of all aspects of the present invention may contain one or more active agents. The porous reservoir and when present the wicking layer is impregnated with any conventionally known active agents, such as, an active agent selected from one or more of an antimicrobial agent, a medicament, a cosmetic a perfume, and a deodorant. In a preferred embodiment of the present invention the active agent is an antimicrobial agent. The active agent may be present in a form selected from form selected from solid, liquid, gel, suspension, emulsion and microencapsulated. Preferably, the active agent will be present in liquid or gel form. The term antimicrobial will be well understood by the person skilled in the art and shall include antibacterial, antifungal and antiviral compositions; and mixtures thereof. The term antibacterial shall include bactericidal and bacteriostatic compositions.

Any conventionally known antimicrobial composition may be used, most preferably, disinfectants are used, for example, alcohols, such as "surgical alcohols", e.g. ethanol, 1-propanol and 2-propanol/isopropanol; chlorhexidine (0.5-4% w/v) including alcoholic formulations, isopropyl alcohol (60-70% v/v), ethyl alcohol (80% v/v) with or without emollients, povidone-iodine (0.75-1%), peroxygen based on potassium peroxomonosulphate or mixtures thereof.

Other antimicrobial compositions which may be mentioned include, quaternary ammonium compounds, such as benzalkonium chloride, iodine, phenol (carbolic acid) compounds, peracetic acid or silver compounds; or mixtures thereof. A preferred antimicrobial composition is an alcohol, such as that commercially available as Cutan® from Deb Limited in the UK. An especially preferred antimicrobial agent has an alcohol content of from 58 to 78% w/w, preferably from 68 to 72% w/w and most preferably alcohol content of 70% w/w.

It is an especially preferred feature of all aspects of the present invention that the device is adapted to remain bacteriostatic, fungistatic and viristatic during its lifetime.

A further preferred antimicrobial agent is one which is capable as acting as bactericidal agent or bacteriostatic agent, e.g. to MRSA. The antibacterial agent is especially a bactericidal agent or a bacteriostatic agent to one or more of MRSA, MSSA, *Necrotizing fasciitis, Escherichia coli*, NorA, *Clostridium difficile, Norovirus, enterococcus faecium* and *pseudomonas aruginosa.* For example, vancomycin, methicillin, etc.

Examples of antifungal agents include, boric acid, or combined antibacterial and antifungal agents, such as triclosan.

The total loading of antimicrobial agent in the porous reservoir layer is dependent upon, inter alia, the form, thickness and density of this layer. This determines the total pore volume or porosity of the layer and therefore its absorbent capacity. The delivery rate may be controlled by the compression resistance of the material used, the total loading of the active agent, e.g. liquid, in conjunction with the properties of the wicking layer when present and the liquid delivery contact layer and the viscosity of the liquid. The latter can be controlled by additives, such as a thickener, if required.

In all aspects of the present invention the liquid delivery contact layer may also be provided with a removable cover layer as protection. Similarly, if the backing layer is provided with an adhesive layer then the adhesive layer and/or the backing layer may also be provided with a cover layer. The removable cover may be, for example, a silicone coated release paper. Alternatively, the whole delivery device may be presented in a sealed package.

The delivery devices of all aspects of the present invention may be made up in a variety of forms. By way of illustration, such forms include, but shall not be limited to, stickers, tapes, pads, tubes, socks and the like. The device may be surface mountable on a vertical surface or any other orientation or surface and may be wrapped around handle form surfaces. Other applications include agricultural pads such as for example foot and mouth infection pads, passenger foot pads at airports, trolley pads on hospital doorways, handles for hospital doorways and all points of patient contact, lifts, handles on buses/trains and other forms of public transport, seats, food preparation surfaces, etc.

The delivery devices of all aspects of the present invention may include an indicator, such as an obsolescence indicator. This may be a time activated indicator or it may be adapted to provide an indication of the internal state of the reservoir layer.

In a further preferred embodiment of the invention we provide a method of preventing the transmission of microorganisms which comprise the use or application of a delivery device as hereinbefore described in each aspect of the present invention.

The invention will now be referred to by the following Figures, which show/represent various forms/states and designs, the invention could take and in which.

Figure 3:
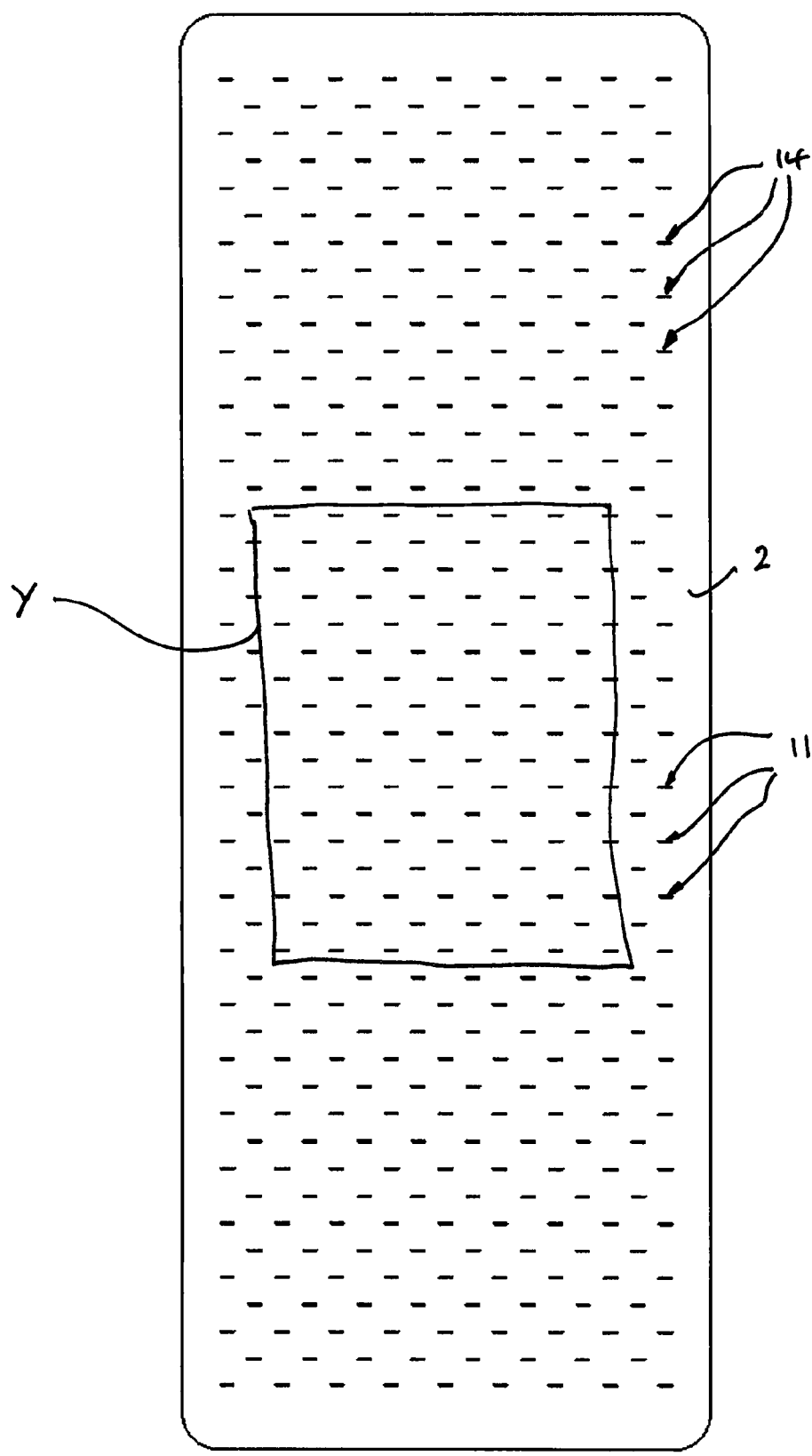
FIG. 3 is front view of a delivery device of the present invention showing the top surface of the liquid delivery contact layer.
Figure 4:
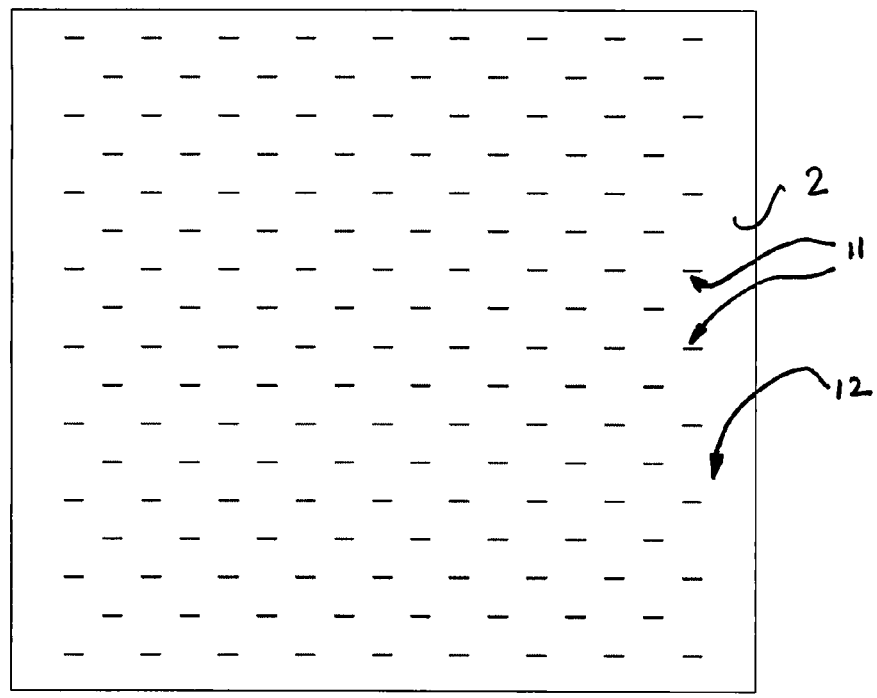
Figure 4:
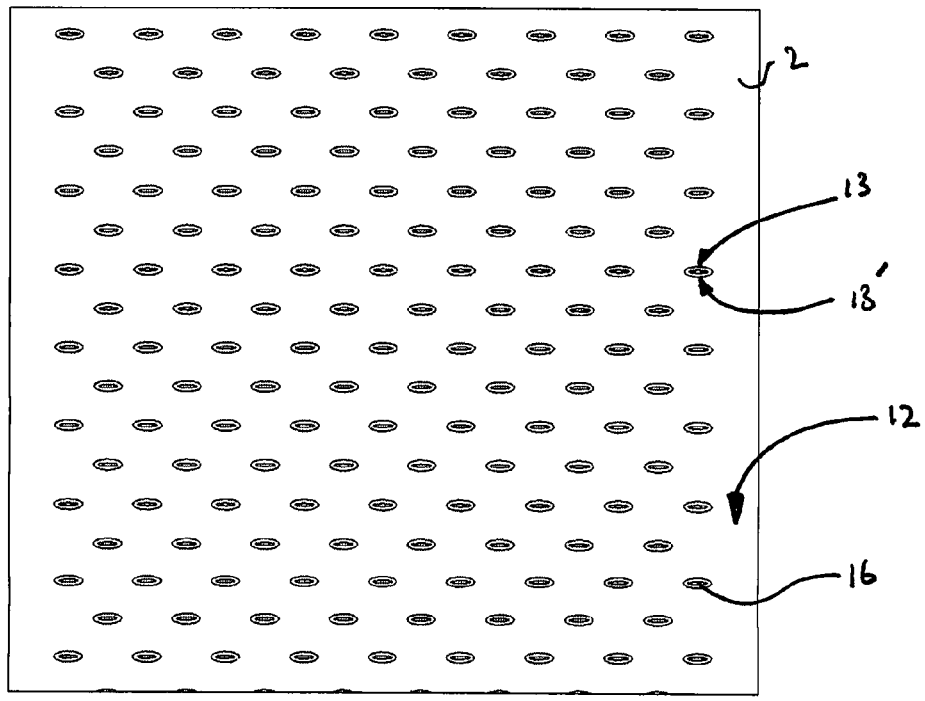

FIGS. 4 (a) and (b) are views of small sections of FIG. 3 before (a) and after compression (b) of the liquid delivery contact layer of a preferred delivery device of the present invention; and FIGS. 5 shows the key stages in manufacture of a liquid delivery contact layer of a preferred delivery device of the present invention having valve like slits and/or pores.

Figure 1:
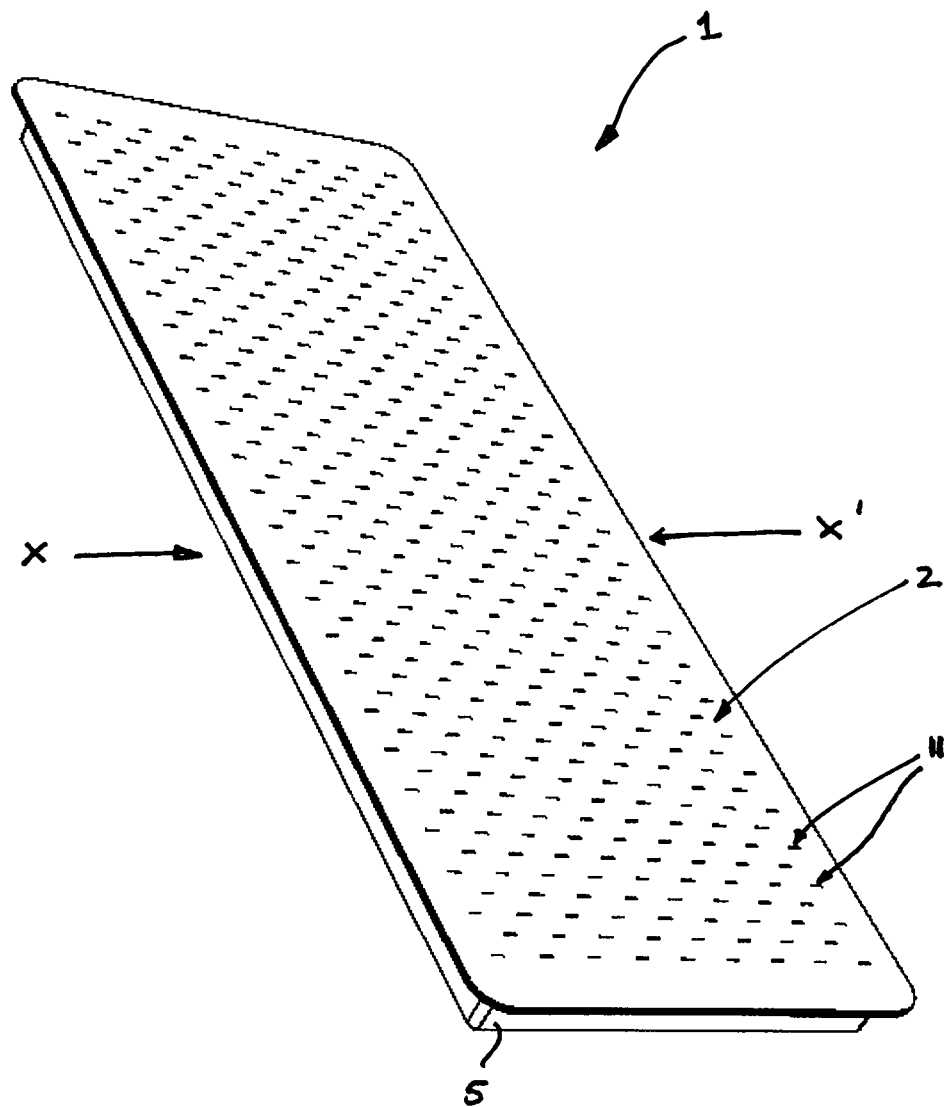
FIG. 1 is a perspective view of a delivery device according to the present invention.
Figure 2:
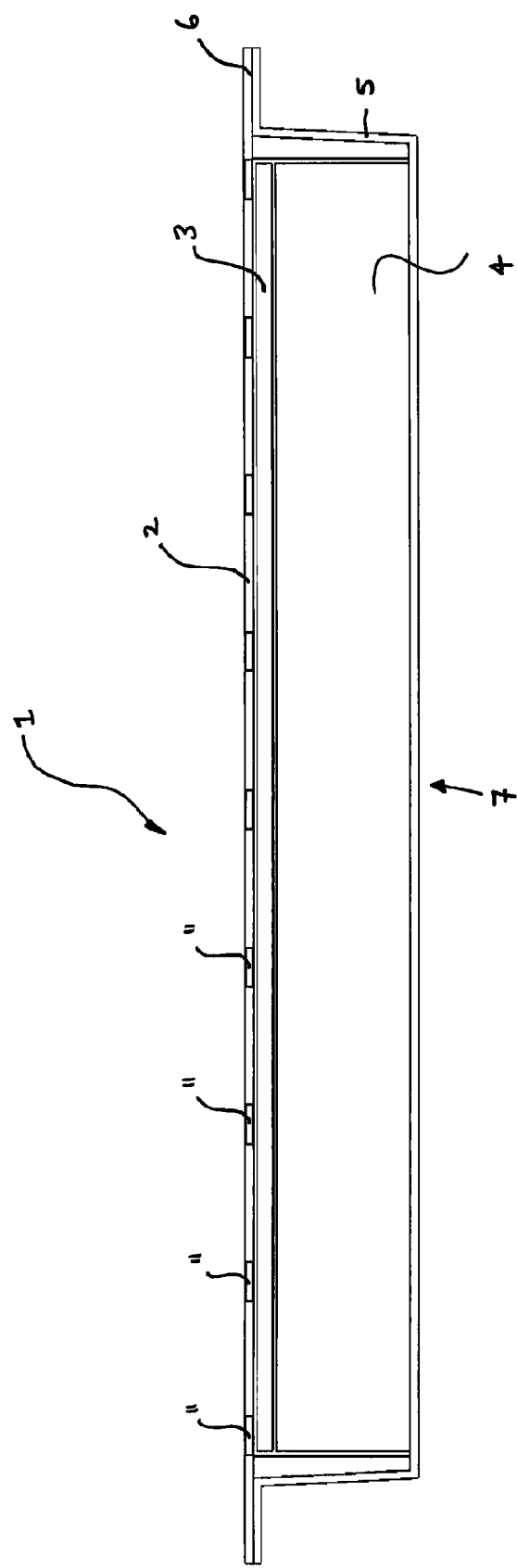
FIG. 2 is a cross-section across plane x, x' of FIG. 1 of a preferred delivery device of the present invention.

With reference to FIGS. 1 and 2 a deliver device (1) comprises a liquid delivery contact layer (2) adjacent to a wicking layer (3), which is adjacent to a porous reservoir layer (4). The wicking payer (3) and the porous reservoir layer (4) are located within a container (5), which is bonded to the liquid delivery contact layer (2) at the periphery (6) of the container (5) and the liquid delivery contact layer (2). The wicking layer (3) and the porous reservoir layer (4) are impregnated with an antimicrobial composition. The device may be attached to a vertical surface (not shown) by applying adhesive to the rear surface (7) of the device.

With reference to FIGS. 3, 4 (a) and (b) there is shown an elastic liquid delivery contact layer (2), before (a) and during (b) compression. FIGS. 4(a) and (b) demonstrate the effect of a localized impact at section Y of FIG. 3. Before compression the slits (11) are closed and any antimicrobial composition is unable to exit through the surfaces (12) of the layer (2) which are impermeable. During compression into the plain of the Figure the layer (2) is elastically deformed and under this deformation the slits (11) proximate to the deformation point and previously closed open and parallel sides (13, 13') separate to define a pore (16) through which any antimicrobial composition may pass through the layer (2). It should be noted that slits (14) that are remote from the point of compression Y are not opened by this mechanism as there are no local transverse forces across these slits (14) to elastically deform the layer (2) proximate to these slits (14). When the compressive force is removed from Y the layer (2) returns elastically to its original state and the parallel sides (13, 13') of the slits (11) close moving adjacent to each other as shown in FIG. 4 (a) and in doing so close the open pore (16).

With reference to FIG. 5 there is shown an elastomeric polyurethane film (1) at various stages (a to e) in the manufacture of an elastic liquid delivery contact layer (10) with valve like slits (11). At stage (a) the film (1) is relaxed. At stage (b) the film (1) has been elongated by 10%. At stage (c) we see the slitting tool (2) being brought into contact with the top surface (3) of the film (1). At stage (d) the slitting tool (2) has been removed and has produced slits (9) that are in the open state as the film (1) is in the extended state. Stage (e) shows the film (1) of stage (d) in the relaxed state and as the final elastic liquid delivery contact layer (10). The open slits (9) have now closed to form valve like slits (11) with the excess material being located at and protruding from the inner surface (4) of the film (1). When the elastic liquid delivery contact layer of stage (e) is stretched the valve like slits (11) will open and the film will be as indicated in stage (d).

The invention claimed is:

1. A delivery device, comprising a reservoir in communication with an elastic liquid delivery contact layer, the elastic liquid delivery contact layer formed of a material having a plurality of closed valve like slits and/or pores extending there through and wherein there is a pre-strain of 0.2% - 5% of the relevant dimension in the contact layer in a direction parallel to the slit length after its integration into the device.

2. The delivery device as claimed in claim 1, wherein the slits are arranged in a parallel fashion either from top to bottom of the device or from side to side of the device within the liquid delivery contact layer.

3. The delivery device as claimed in claim 1, wherein the material of the liquid delivery contact layer is a non-permeable non-porous elastomeric material.

4. The delivery device as claimed in claim 1, wherein the liquid delivery contact layer material is manufactured from an elastomeric film of polymeric material.

5. The delivery device as claimed in claim 4, wherein the elastomeric material has a maximum extension that is below the elastic limit of the layer material in order that on release of the force, up to 100% elastic recovery takes place so that the original positions of the slit edges are regained.

6. The delivery device as claimed in claim 4, wherein the elastomeric material has an elastic recovery of >75% at 1% extension.

7. The delivery device as claimed in claim 4, wherein the elastomeric film exhibits a maximum extension of 500%-850% and a peak load at 20% extension of between 5 to 15N/25mm.

8. The delivery device as claimed in claim 4, wherein the breaking load of the film is not less than 20 N/25mm.

9. The delivery device as claimed in claim 1, wherein the material used as the elastic liquid delivery contact layer is a polyurethane.

10. The delivery device as claimed in claim 1, wherein the material used as the elastic liquid delivery contact layer is a thermoplastic polyester elastomeric film having a Shore D hardness of >60.

11. The delivery device as claimed in claim 1, wherein the number of slits and/or pores per square area in the elastic layer is between 40 to 150 slits and/or pores/in$^2$ (6.2 to 23.3 slits and/or pores/cm$^2$).

12. The delivery device as claimed in claim 1, wherein the slit length is 5 mm or less.

13. The delivery device, as claimed in claim 1, comprising a reservoir of porous material in communication with a liquid delivery contact layer, wherein the reservoir material has a compression modulus within the range of 150 to 650 $N \cdot m^{-2} \cdot \Delta mm^{-1}$.

14. The delivery device as claimed in claim 13, wherein the porous reservoir material comprises a woven material, a nonwoven material, an open cell foam, or any combination of two or more of these materials.

15. The delivery device as claimed in claim 13, wherein the reservoir material comprises a hydrophilic polyurethane open cell foam.

16. The delivery device as claimed in claim 15, wherein the reservoir material comprises a hydrophilic polyurethane thermoset foam.

17. The delivery device as claimed in claim 13, wherein the foam is a low-density, open-cell, thermoplastic, absorbent foam, comprising at least two of the groups consisting of: a base resin, a surfactant, a thermoplastic elastomer, and a plasticizing agent.

18. The delivery device as claimed in claim 13, wherein the reservoir material has a void fraction of greater than 80%, preferably greater than 85% and most preferably greater than 90% as determined by gas pycnometry.

19. The delivery device as claimed in claim 13, wherein the reservoir material has a density of 0.2 g cm$^{-3}$ or less as determined by ASTM D1622-98.

20. The delivery device as claimed in claim 13, wherein the total thickness of the material comprising the reservoir is less than 12 mm.

21. The delivery device as claimed in claim 13, wherein the porous reservoir material has a resiliency as determined by ASTM D3575 of greater than 85%.

22. The delivery device as claimed in claim 13, wherein the porous reservoir material exhibits a percentage strain as measured at 6.8 KPa by the method described in ASTM D3575 of 30% or less.

23. The delivery device as claimed in claim 1, comprising a reservoir in communication with a wicking layer separating the reservoir from a liquid delivery contact layer in communication with the wicking layer.

24. The delivery device as claimed in claim 23, wherein the wicking layer comprises porous material.

25. The delivery device as claimed in claim 23, wherein the wicking layer comprises a woven or nonwoven fabric.

26. The delivery device as claimed in claim 23, wherein the wicking layer comprises a nonwoven fabric manufactured using drylaid web formation.

27. The delivery device as claimed in claim 26, wherein the wicking layer comprises parallel laid webs.

28. The delivery device as claimed in claim 27, wherein the parallel laid webs are bonded via mechanical bonding.

29. The delivery device as claimed in claim 28, wherein the bonding is via hydroentangling, needlepunching or combinations thereof.

30. The delivery device as claimed in claim 23, wherein the porous material of the wicking layer is preferably comprised of a pore structure that is capable of retaining and distributing in-plane (i.e. in the x and y planes), the cleaning fluid/gel by means of capillary forces.

31. The delivery device as claimed in claim 23, wherein the porous material of the wicking layer is such that it restricts or moderates the total volume of cleaning fluid/gel that may be evacuated from the reservoir and passed transversely through the wicking layer and to the exterior of the device via the liquid delivery contact layer.

32. The delivery device as claimed in claim 23, wherein the wicking layer comprises fibre surfaces that are wettable.

33. The delivery device as claimed in claim 23, wherein the wicking layer has a sessile drop angle of less than 90°.

34. The delivery device as claimed in claim 23, wherein the wicking materials is one or more materials selected from the group consisting of regenerated cellulose (specifically viscose, wood pulp, lyocell or Tencel®), plasma-treated aromatic and aliphatic polyesters and polyolefins.

35. The delivery device as claimed in claim 23, wherein the wicking material is a nonwoven fabric comprised of 100% Tencel® fibre prepared by carding, cross-lapping and needle punching.

36. The delivery device as claimed in claim 23, wherein the wicking layer has a mean thickness of between 0.5 and 2.0 mm.

37. The delivery device as claimed in claim 25, wherein the nonwoven fabric has a bubble point pore diameter of between 50 to 100 µm.

38. The delivery device as claimed in claim 25, wherein the nonwoven fabric has a mean flow pore diameter of between 15 and 30 µm.

39. The delivery device as claimed in claim 1, wherein the elastic liquid delivery contact layer having a plurality of closed slits and/or pores is manufactured by a method comprising applying a strain to an elastomeric material in the x, y plane, while the elastomeric material is under strain inducing a plurality of pores and/or slits through the elastomeric material, and removing the applied strain to enable the elastomeric material to elastically recover and providing closed pores and/or slits with material associated with the closed pore and/or slits protruding from a surface of the elastomeric film.

\* \* \* \* \*